US010925562B2

(12) United States Patent
Mc Carthy et al.

(10) Patent No.: US 10,925,562 B2
(45) Date of Patent: Feb. 23, 2021

(54) VARIABLE SID IMAGING

(71) Applicant: General Electric Company, Schenectady, NY (US)

(72) Inventors: Thomas Mc Carthy, Buc (FR); Gregoire Avignon, Buc (FR)

(73) Assignee: General Electric Company, Schenectady, NY (US)

( * ) Notice: Subject to any disclaimer, the term of this patent is extended or adjusted under 35 U.S.C. 154(b) by 738 days.

(21) Appl. No.: 15/439,267

(22) Filed: Feb. 22, 2017

(65) Prior Publication Data

US 2018/0235559 A1    Aug. 23, 2018

(51) Int. Cl.
| | |
|---|---|
| *A61B 6/00* | (2006.01) |
| *A61B 6/10* | (2006.01) |
| *A61B 6/04* | (2006.01) |
| *A61B 6/06* | (2006.01) |
| *A61B 6/02* | (2006.01) |
| *A61B 5/107* | (2006.01) |

(52) U.S. Cl.
CPC ............ *A61B 6/4452* (2013.01); *A61B 6/027* (2013.01); *A61B 6/0407* (2013.01); *A61B 6/0487* (2020.08); *A61B 6/06* (2013.01); *A61B 6/10* (2013.01); *A61B 6/4085* (2013.01); *A61B 6/4429* (2013.01); *A61B 6/4476* (2013.01); *A61B 6/469* (2013.01); *A61B 6/488* (2013.01); *A61B 6/544* (2013.01); *A61B 6/545* (2013.01); *A61B 6/547* (2013.01); *A61B 6/588* (2013.01); *A61B 6/589* (2013.01); *A61B 5/1079* (2013.01)

(58) Field of Classification Search
CPC ................................ A61B 6/588; A61B 6/545
See application file for complete search history.

(56) References Cited

U.S. PATENT DOCUMENTS

| | | | |
|---|---|---|---|
| 2001/0036246 A1 | 11/2001 | Graumann | |
| 2003/0099328 A1 | 5/2003 | Jensen et al. | |
| 2005/0117703 A1 | 6/2005 | Oota | |
| 2006/0222143 A1 | 10/2006 | Du et al. | |
| 2007/0106154 A1* | 5/2007 | Conti | G01T 1/1611 |
| | | | 600/436 |

(Continued)

FOREIGN PATENT DOCUMENTS

| | | |
|---|---|---|
| WO | 2015/132069 A1 | 9/2015 |
| WO | 2017/058345 A1 | 4/2017 |

OTHER PUBLICATIONS

Extended European Search Report and Opinion issued in connection with corresponding EP Application No. 18158084.6 dated Jul. 9, 2018.

*Primary Examiner* — Dani Fox

(57) ABSTRACT

A system for imaging includes a gantry movable relative to a subject. A source is configured to emit radiation during an imaging procedure. A detector is configured to receive attenuated radiation from the source during an imaging procedure, at least one of the source and the detector movably secured to the gantry by an adjustable joint. An imaging controller is operably connected to at least the gantry and to the adjustable joint, wherein the gantry controller receives a priori patient information and imaging system geometry information, the imaging controller determines an imaging geometry and operates the gantry and the adjustable joint to vary a source to image-receptor distance (SID) according to the imaging geometry.

19 Claims, 8 Drawing Sheets

(56) References Cited

U.S. PATENT DOCUMENTS

2012/0300910 A1* 11/2012 Gorges ................ A61B 6/4429
378/198
2015/0228071 A1 8/2015 Jockel et al.

* cited by examiner

VARIABLE SID IMAGING

BACKGROUND

The present disclosure is related to the field of imaging. More specifically the present disclosure is directed to systems and methods of medical imaging with variable source to image detector distances.

In medical x-ray imaging, for example, angiographic systems, an x-ray source and an x-ray detector are generally mounted on opposing ends of a substantially C-shaped gantry such that x-rays emitted by the source in a cone-shaped beam are incident on and detectable by the x-ray detector, although other configurations of x-ray imaging systems are known. The source and the detector are positioned such that when an object (e.g., part of a human body) is interposed there between and is irradiated with x-rays, the detector produces data representative of characteristics of the interposed object. The data produced is typically displayed on a monitor or electronically stored.

The C-arm gantry defines an axis of rotation about which the source and detector are rotatable. By positioning this axis of rotation at or near an object, and by rotating the source and detector about the object, or rotating the object about the source and detector, images of the object taken at a plurality of different orientations can be obtained. These images can be combined to generate a comprehensive three-dimensional image of the object, for example using methods of image reconstruction. Such acquisitions are usually called cone-beam computed tomography (CBCT) acquisitions.

CBCT capable systems typically provide a small field of view and thus can only 3D image a small portion of an object (e.g. patient) during a single scan. When imaging an off-center portion of an object, for example, a liver of a patient, the table upon which the patient rests during the scan is typically positioned such that the anatomy of interest coincides with the 3D field of view. However, it is possible that the detector and/or the source may collide with the patient because the patient is now positioned closer to the trajectories of the detector and/or the source. Moving the detector away from the center of the rotation reduces collision risk, but further reduces the diameter of any reconstructed three-dimensional image of the object. Currently, imaging system operators use a trial-and-error approach wherein the patient is repositioned so that no such collisions occur. In some instances, repositioning the patient may lead to the anatomy of interest lying outside of the imaging field of view. Reduced field of view or improper patient positioning can potentially lead to additional acquisition, resulting in increased x-ray dose, prolonged medical procedure and/or additional use of chemical injectable agent.

BRIEF DISCLOSURE

An exemplary embodiment of a system for medical imaging includes a gantry movable about a patient to be imaged. A source is configured to emit radiation during an imaging procedure. A detector is configured to receive attenuated radiation from the source during the imaging procedure. At least one of the source and the detector is movably secured to the gantry by an adjustable joint. A gantry controller is operably connected to at least the gantry and to the adjustable joint. The gantry controller receives a priori patient information and imaging system geometry information. The gantry controller determines an imaging geometry. The gantry controller operates the gantry and the adjustable joint during an imaging procedure to vary a source to image-receptor distance (SID) according to the imaging geometry.

An exemplary embodiment of a method of medical imaging includes obtaining patient information. A field of view (FOV) is determined for an imaging procedure at least in part according to the patient information. An imaging geometry is determined at least in part based upon the FOV and the patient information. The imaging geometry includes at least one of an emitter trajectory and a detector trajectory with a variable source to image-receptor distance (SID) between the emitter trajectory and the detector trajectory. The FOV is evaluated by applying at least one FOV optimization criteria to the FOV. The FOV is adjusted to a volume of interest according to the evaluation of the FOV. The imaging geometry is adjusted to the adjusted FOV.

BRIEF DESCRIPTION OF THE DRAWINGS

The present invention will be better understood from reading the following description of non-limiting embodiments, with reference to the attached drawings, wherein below.

DETAILED DISCLOSURE

Figure 1:
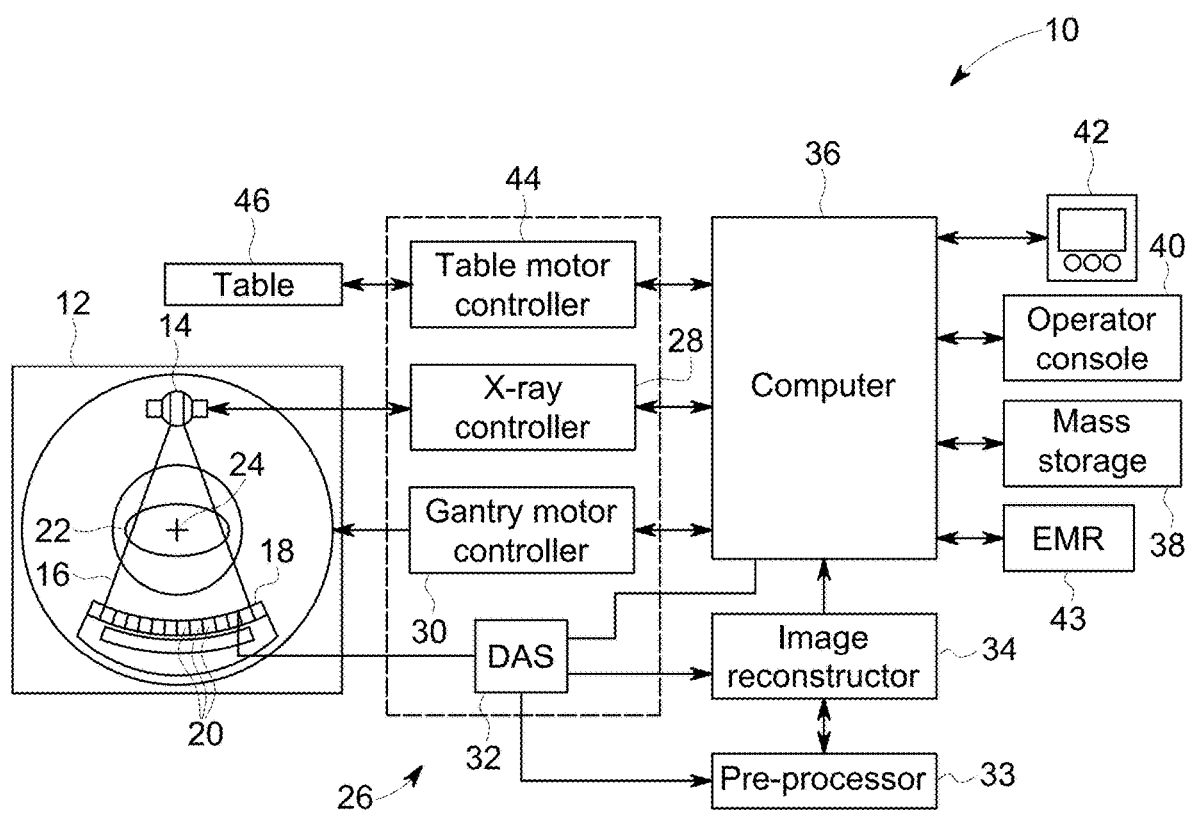
FIG. 1 is a block schematic diagram of an exemplary imaging system according to an embodiment of the invention.

The following description relates to various embodiments of medical imaging systems. In particular, methods and systems are provided for improved imaging in a computed tomography (CT) imaging system. An example of a CT imaging system that may be used to acquire images processed in accordance with the present techniques is provided in FIG. 1. Though a CT system is described by way of example, it should be understood that the present techniques may also be useful when applied to images acquired using other imaging modalities, such as tomosynthesis, MRI, PET, SPECT, C-arm angiography, mammography ultrasound, and so forth. The present discussion of a CT imaging modality is provided merely as an example of one suitable imaging modality. For example, a CT system in a C-arm configuration, such as the system depicted in FIG. 2, includes a source and a detector mounted opposite to each other on the ends of a substantially C-shaped or semi-circular gantry, or C-arm, thereby defining an imaging plane with an isocenter. It will be recognized that in other imaging systems within the present disclosure, one of the source or detector may remain in a fixed position while the other of the source or detector is movable with respect to the patient. During an image acquisition, the C-arm may rotate the source and the detector about an axis of rotation, which may coincide with the isocenter. Typically, a subject to be imaged, such as a patient, is positioned within the imaging plane such that radiation generated by the source passes through the subject and is detected by the detector. For cone beam CT (CBCT), the field of view (FOV) of the imaging system is small and centered on the isocenter. In some instances, the region of interest (ROI), which may exemplarily be a particular organ, organ system, or object to be imaged, may be off-center with respect to the subject, and so the subject should be positioned such that the FOV coincides with the ROI.

In CBCT and in other imaging modalities, the FOV may of equivalent size or smaller than the ROI. The FOV and image quality may exemplarily be dependent, at least in part upon the relative positions of components within the imaging system. As exemplarily depicted in FIG. 2, these include a distance between the source and the detector (SID), the distance between the source and the center of the ROI (SOD) and the distance between the detector and the center of the ROI (OID). To increase the FOV, one may decrease the OID and increase the SOD. However, the patient's body, or other object supporting the patient, the imaging system itself, and/or the arrangement of the imaging room may create further constraints on the positions of the source and detector. This is particularly true if the ROI is off-center with respect to a rotation axis about the patient. In embodiments as disclosed in further detail herein, improved imaging can be obtained by varying the positions of the source and/or the detector during an imaging procedure. The positions of the source and/or the detector can be varied in consideration of both the ROI and the geometry of the imaging system itself.

Figure 2:
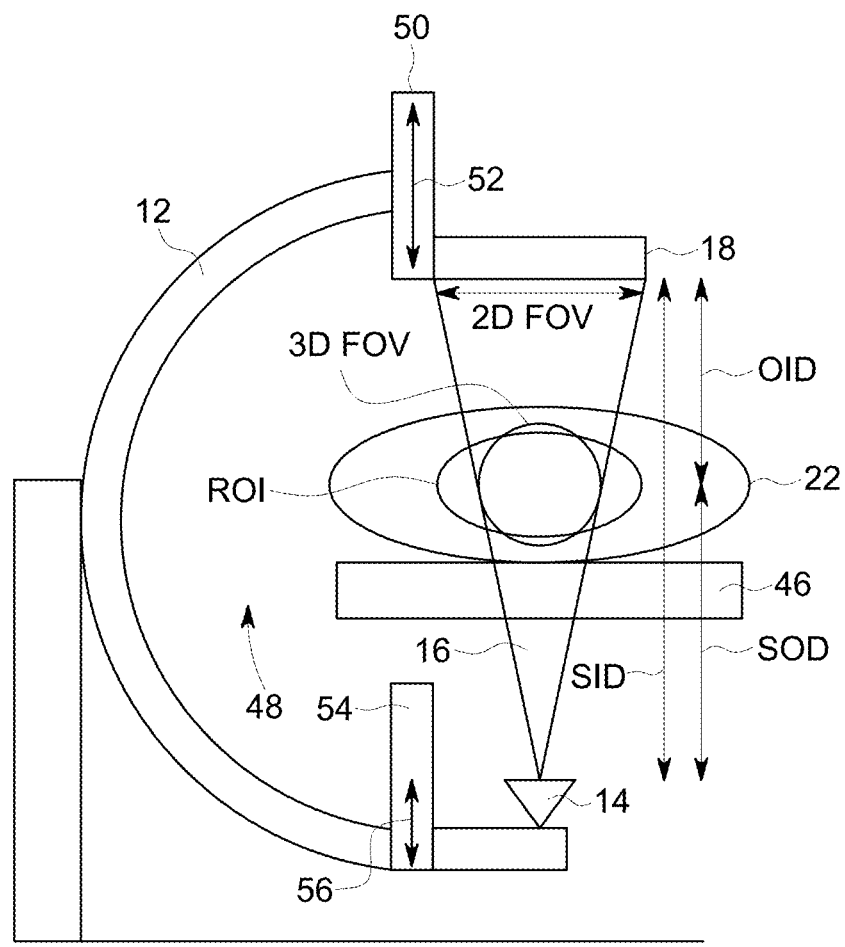
FIG. 2 is a schematic diagram of a C-arm assembly according to an embodiment of the invention.

Referring to FIG. 1, a CT imaging system 10 is shown as including a gantry 12. In some examples, CT system 10 may be an energy integrating, a photon counting (PC), or a photon energy discriminating (ED) CT detector system. Gantry 12 includes an x-ray source 14 that projects a beam of x-rays 16 toward detector array 18. The x-rays pass through a subject 22, such as a patient, to generate attenuated x-rays. In an alternative embodiment, each detector element 20 of detector array 18 may be a photon energy integrating detector, a photon counting detector, or a photon energy discriminating detector. Each detector element 20 produces an electrical signal that represents an intensity of the attenuated x-rays. During a scan to acquire projection data, gantry 12 and components mounted on gantry 12 rotate about a center of rotation 24.

Rotation of a gantry 12 and an operation of x-ray source 14 are governed by a imaging controller 26 of CT system 10. Imaging controller 26 includes an x-ray controller 28 that provides power and timing signals to x-ray source 14, and a gantry motor controller 30 that controls a rotational speed and position of gantry 12. In some embodiments, gantry motor controller 30 may control a tilt angle of gantry 12. The gantry motor controller 30 may further operate to control a movable joint 50 between the detector 18 and the gantry 12. A data acquisition system (DAS) 32 in imaging controller 26 samples and digitizes the projection data from detector elements 20 and converts the projection data to sampled and digitized projection data for subsequent processing. In some embodiments, DAS 32 may be positioned adjacent to detector array 18 on gantry 12.

Pre-processor 33 receives the sampled and digitized projection data from DAS 32 to pre-process the sampled and digitized projection data. In one embodiment, pre-processing includes, but is not limited to, an offset correction, a primary speed correction, a reference channel correction, an air-calibration, and/or applying a negative logarithmic operation. As used herein, the term processor is not limited to just those integrated circuits referred to in the art as a processor, but broadly refers to a controller, a microcontroller, a microcomputer, a programmable logic controller, an application specific integrated circuit, and any other programmable circuit, and these terms are used interchangeably herein. Pre-processor 33 pre-processes the sampled and digitized projection data to generate pre-processed projection data.

An image reconstructor 34 receives the pre-processed projection data from pre-processor 33 and performs image reconstruction, such as filtered back-projection (FBP), to generate a reconstructed image. The reconstructed image is applied as an input to a computer 36 which stores the reconstructed image in a mass storage device 38, where the mass storage device 38 may include, as non-limiting examples, a hard disk drive, a floppy disk drive, a compact disk-read/write (CD-R/W) drive, a Digital Versatile Disc (DVD) drive, a flash drive, and/or a solid-state storage device. As used herein, the term computer is not limited to just those integrated circuits referred to in the art as a computer, but broadly refers to a processor, a microcontroller, a microcomputer, a programmable logic controller, an application specific integrated circuit, and any other programmable circuit, and these terms are used interchangeably herein. An x-ray controller 28 adjusts a tube current within x-ray source 14 based on a quality of the reconstructed image.

Computer 36 also receives commands and scanning parameters from a user, such as an operator, via a console 40 that includes a user interface device, such as a keyboard, mouse, voice-activated controller, touchscreen or any other suitable input apparatus. An associated display 42 allows a user, such as an operator, to observe the reconstructed image and other data from computer 36. The commands and scanning parameters are used by computer 36 to provide control signals and information the imaging controller 26, including the DAS 32, x-ray controller 28, and gantry motor controller 30. In addition, computer 36 may operate a table motor controller 44 exemplarily of the imaging controller 26 which controls a movable subject support, which is exemplarily a motorized table 46, to position subject 22 within gantry 12. Particularly, table motor controller 44 adjusts table 46 to move portions of subject 22 and center the subject 22 in a gantry opening 48. In some examples, the gantry may be motorized and the table may be fixed. In some more examples, multiple gantries may be used.

As described in further detail herein, the gantry motor controller 30, for example under operation from the computer 36, may further operate to control a movable joint 50 between the detector 18 and gantry 12. The movable joint 50 is operated by the gantry motor controller 30 to move the position of the detector exemplarily towards and away from a center point of the gantry 12 along line 52. Similarly, the gantry motor controller 30 may operate a movable joint 54 between the source 14 and the gantry 12. The movable joint 52 is operated by the gantry motor controller 30 to move the position of the source 14 exemplarily towards and away from a center point of the gantry 12 along line 56. The movable joints 50, 54 may be any of a variety of mechanical movable joints, including, but not limited to rack-and-pinion, screw, or chain driven actuators. Operation of the movable joints 50, 54 control the effective gantry opening 48 and also the SID, SOD, and OID and described in further detail herein. It will be recognized that in still further embodiments, adjustable SID, SOD, and OID may exemplarily be provided by independently driving the source and the detector, for example, in a system without a c-arm physically connecting the source and the detector. In another exemplary embodiment, the at least one moveable joint may be provided on the gantry 12, e.g. c-arm, such movable joint being operable to adjust the relative position between the source 14 and the detector 18.

In embodiments, the computer 36 may additionally comprise or operate all or part of the imaging controller 26, including, but not limited to the x-ray controller 28, gantry motor controller 30, DAS 32, pre-processor 33, image reconstructor 34, and table motor controller 44. It will be recognized that these components may be implemented in one or more processors or controllers and perform the functions as described herein in coordination among such controllers or as modules or programs operating on a single computer or controller.

In an alternative embodiment, a high frequency electromagnetic energy projection source configured to project high frequency electromagnetic energy toward subject 22 may be used instead of x-ray source 14. A detector array disposed within a gantry and configured to detect the high frequency electromagnetic energy may also be used instead of detector array 18.

In one embodiment, the image reconstructor 34 stores the reconstructed images in the mass storage device 38. Alternatively, the image reconstructor 34 transmits the reconstructed images to the computer 36 for generating useful patient information for diagnosis and evaluation. In certain embodiments, the computer 36 transmits the reconstructed images and/or the patient information to a display 42 communicatively coupled to the computer 36 and/or the image reconstructor 34. In some embodiments, patient information may be collected from an external source, possibly electronically, for example, as stored in an Electronic Medical Record (EMR) 43 and may also be entered by the operator of the machine.

In one embodiment, the display 42 allows the operator to evaluate the imaged anatomy. The display 42 may also allow the operator to select an ROI and/or request patient information, for example, via graphical user interface (GUI) for a subsequent scan or processing.

Figure 3A:
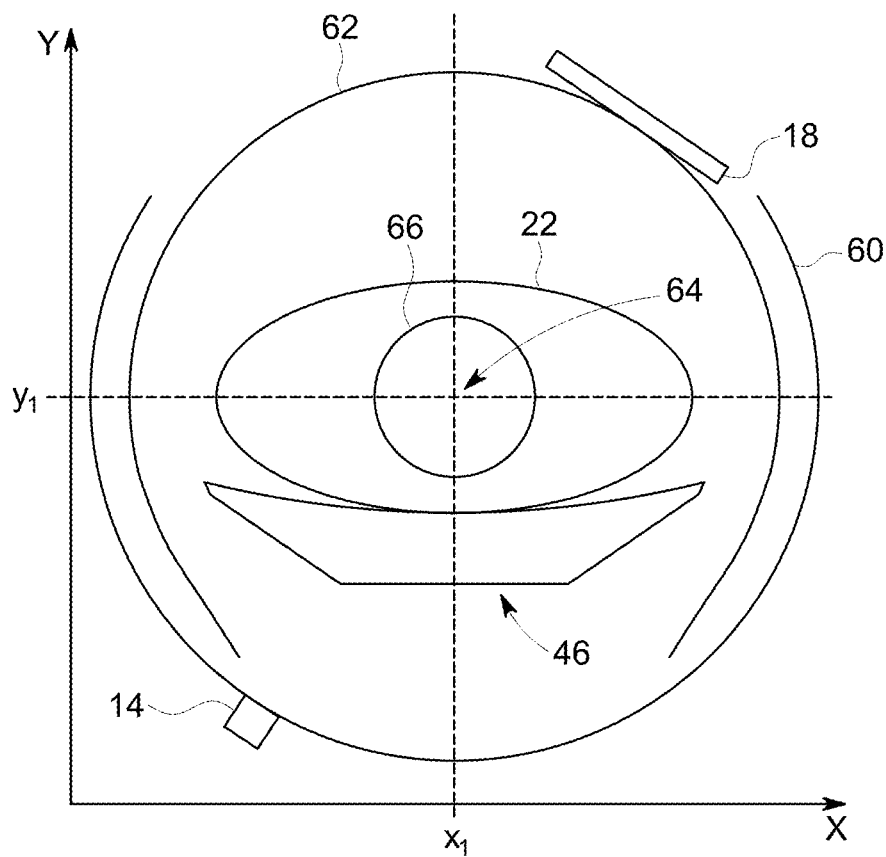
FIGS. 3A and 3B diagrammatically depict source and detector trajectories of imaging geometries with respect to a subject.
Figure 3B:
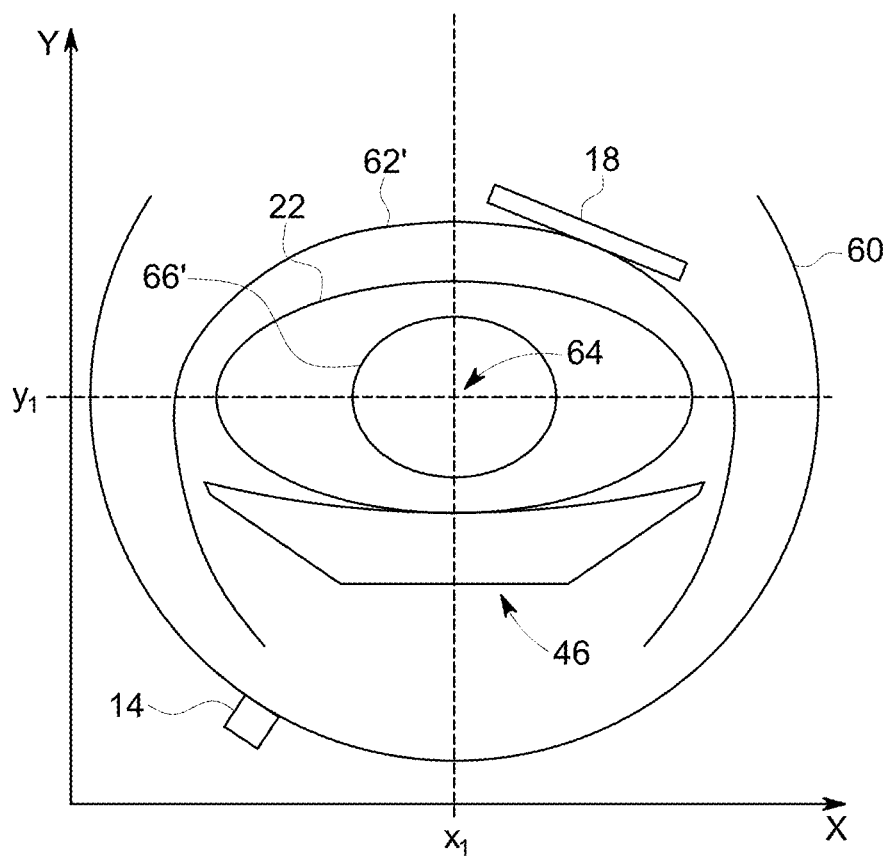

FIGS. 3A and 3B diagrammatically depicts exemplary imaging geometries between a source trajectory and a detector trajectory with respect to a subject. FIGS. 3A and 3B exemplarily represent the patient 22 positioned on the movable table 46. By operation of the gantry as explained above, the x-ray source 14 is movable along a source trajectory 60 and a detector 18 is movable along a detector trajectory 62. In FIG. 3A, the patient 22 is located centrally to the source trajectory 60 and to the detector trajectory 62. In FIG. 3B, the detector trajectory 62' is modified to follow a contour of the movable table 46 and the patient 22. In such a detector trajectory 62', the OID distance is reduced without risking collision between the detector 18 and either the patient 22 or the table 46. It will be recognized that in exemplary embodiments, due to the mechanical arrangement of the gantry that the source 14 and the detector 18 are held in opposition to one another and coordinately rotate about their respective source trajectory 60 and detector trajectory 62, 62'. In the example depicted in FIG. 3A, the coordinated and symmetrical shape of the source trajectory 60 and the detector trajectory 62 provides an FOV 66, in this case exemplarily a three-dimensional reconstruction FOV, centered on an isocenter 64 of the source trajectory 60 and detector trajectory 62. However, as noted above, in medical imaging generally, and exemplarily in 3D medical imaging more specifically, the FOV produced in this manner may be smaller than or of equivalent size to the full width of the patient at the location of the region of interest to be imaged furthermore, as the isocenter of the imaging is offset (in either the x dimension and/or y dimension) within the patient 22, geometric constraints of the imaging system may impact the available trajectories for the x-ray source trajectory 60 and the detector trajectory 62. As will be described in further detail with respect to FIGS. 4 and 5, the imaging system 10 and methods of imaging can be used to improve the correspondence between the ROI and the FOV during an imaging procedure. While the systems and method as described herein may have utility with respect to 2D imaging, particular further advantages may be achieved with respect to 3D imaging.

Figure 4:
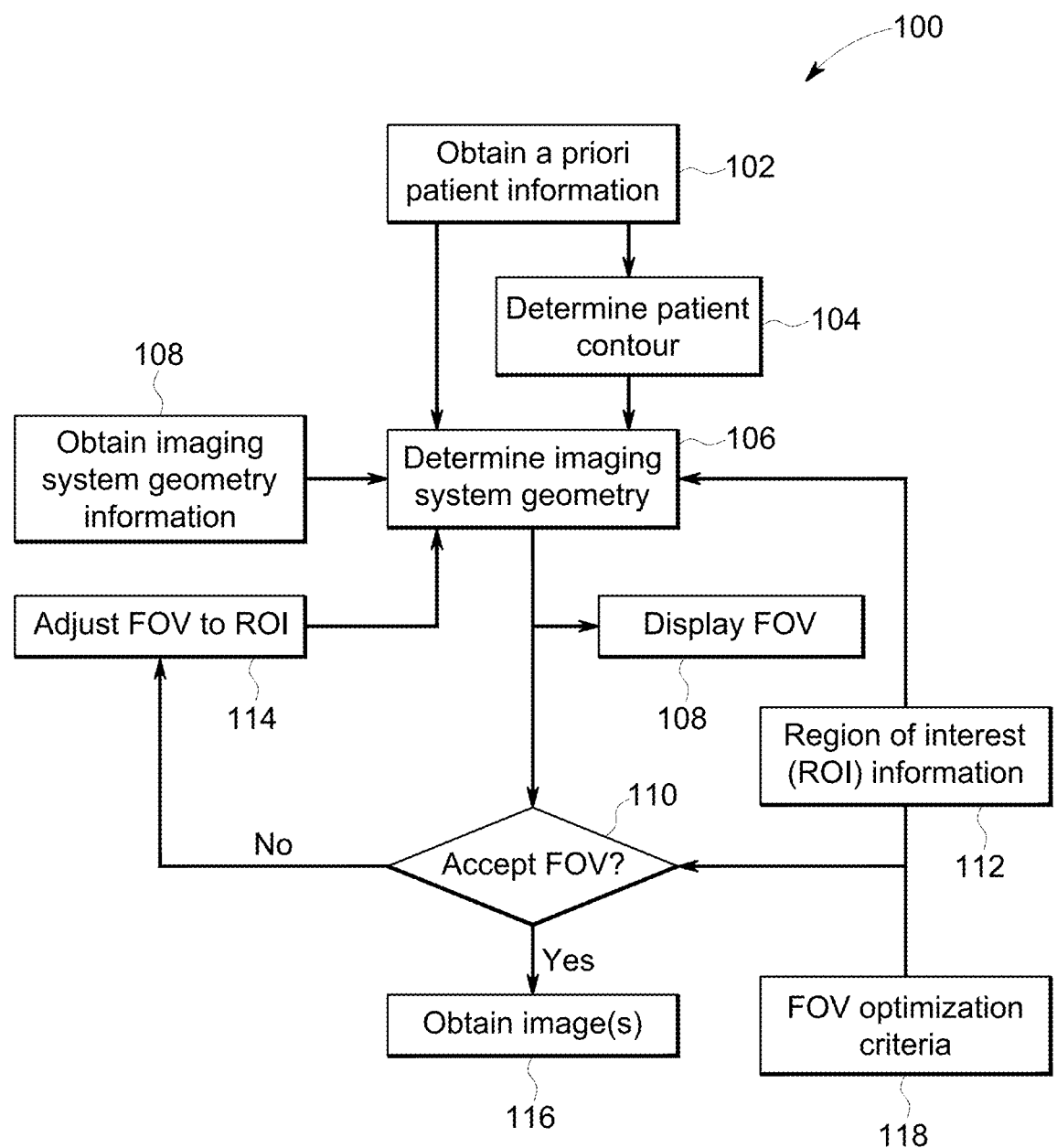
FIG. 4 is a flow chart that depicts an exemplary embodiment of a method of variable SID imaging.

FIG. 4 is a flow chart that depicts an exemplary embodiment of a method 100 of variable SID imaging. The method 100 begins by obtaining a priori patient information 102. The a priori information is information regarding the patient obtained prior to the imaging procedure. The a priori patient information obtained may include previously acquired medical image information, for example a diagnostic CT image of a patient, distance data as may be acquired from a scout scan using low or no x-ray dose scout scanning, and in an example may detect the position of sensors located in the table and/or on the patient with respect to the source and/or detector rather than using x-ray radiation. Such a scout image may be used to detect a patient contour. Additionally, the a priori information may include patient physiological information, including age, height, weight, patient body mass index (BMI), or other measurements such as, but not limited to shoulder width, chest circumference, waist circumference, and head circumference. In a still further exemplary embodiment, the a priori information may include a patient model which may be a generalized or predetermined model, for example a model which may include generalized dimensions and parameters for example based upon patient physiological measurement.

Optionally, at 104, a patient contour at the imaging plane is determined. As noted above, the patient contour may exemplarily be obtained from a scout image taken of the image, or may be represented as a model of the patient. In a still further exemplary embodiment, a model of the patient, for example a model based upon physiological information of the patient may be registered to the actual patient at the time of the imaging procedure, for example by registration of the patient model to a scout image or registration of a patient model to obtained patient position information.

At 106 imaging system geometry is determined. In an exemplary embodiment, the imaging system geometry includes at least one of an x-ray source trajectory, a detector trajectory, and a table position. In further exemplary embodiments, the imaging system geometry includes all three of these parameters, as will be described in further detail herein.

Determining the image system geometry may further include obtaining image system geometry information at 108. The image system geometry information may be obtained either from inputs of a clinician or technician operating the imaging system, or may be predetermined and stored with respect to a particular imaging system and accessed from such a storage of computer data at a computer readable medium. The imaging system geometry information may include further information, measurement, and/or constraints on the imaging system geometry. In exemplary embodiments, the imaging system geometry information may include, for example, the dimensions of the gantry and/or c-arm of the gantry including, the positions of the x-ray source and detector. The imaging system geometry information may further include the range of SID achievable by the gantry as well as the ranges of positions to which each of the x-ray source and the detector are movable. The imaging system geometry information may further include information regarding the dimensions and position of the table and also the movement of the table and positions to which the table may be moved. In a still further exemplary embodiment, if the movement of the gantry is further limited by the position of other objects in association with the imaging system, the positions and/or dimensions of these objects may also be included in the imaging system geometry information. This may include, but need not be limited to a position of a floor, walls, or other pieces of medical equipment, for example other pieces of imaging or surgical equipment positioned around the patient. These additional physical constraints on the gantry movement may be considered in order to avoid collision of a portion of the gantry with these other objects. Sensors located on the medical or surgical equipment used to detect relative locations and positions may be used. In other embodiments, locations of walls, floors, or other objects may be input and stored as part of a configuration process. In a still further exemplary embodiment, the imaging system geometry information may further include predefined or predetermined trajectory for the x-ray source and/or the detector. Such exemplary predefined trajectory may, for example, represent trajectories which consider generalized body types (e.g. thin, average, large) exemplary positions of the patient relative to the gantry isocenter (e.g. centered, left off set, right off set), and/or generalized source and detector position (minimum SID, maximum SID, average SID).

In an exemplary embodiment, a user, for example a clinician or technician, may select one of these default trajectories from which the method beings, the determination of the imaging system geometry at 106. In an automated embodiment, an initial trajectory, for example a trajectory with a maximum SID within the constraints of any other physical objects relative to the imaging system, may be used to begin the determination at 106. In an exemplary embodiment, the imaging system geometry determined at 106 may exemplarily initially provide a table position and a initial source trajectory and a detector trajectory about the patient. In an exemplary embodiment, this may exemplarily be as depicted in FIG. 3.

Exemplary embodiments as described herein may be implemented in automatic or semi-automatic embodiments. In a semi-automatic implementation, further input from the user (e.g. clinician or technician) of the imaging system is provided to add additional user input into the imaging system geometry by evaluating the field of view in relation to the region of interest. The user provides this input through a user interface which incorporates a graphical display and a user input device whereby the user can view the determined imaging system geometry in relation to the region of interest and the current field of view resulting from the imaging system geometry. In an automated implementation, the determination of imaging system geometry incorporates region of interest information, which may in part be provided by the clinician and/or stored in a digital file, for example of a patient's electronic medical record (EMR) or obtained by way of imaging analysis of one or more acquired medical images. It will be recognized that both of these implementations are considered to be within the scope of the present disclosure as well as other implementations of these features as would be recognized by a person of ordinary skill in the art in view of the present disclosure.

Figure 5A:
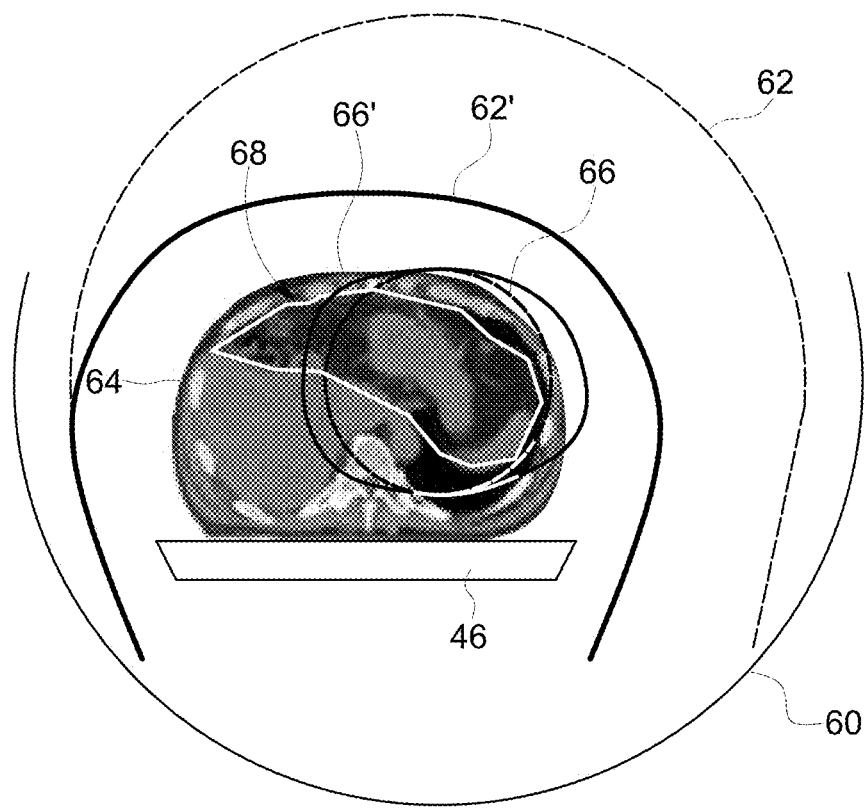
FIGS. 5A-D diagrammatically depict operation of exemplary embodiments of the system operation and field of view modifications.
Figure 5B:
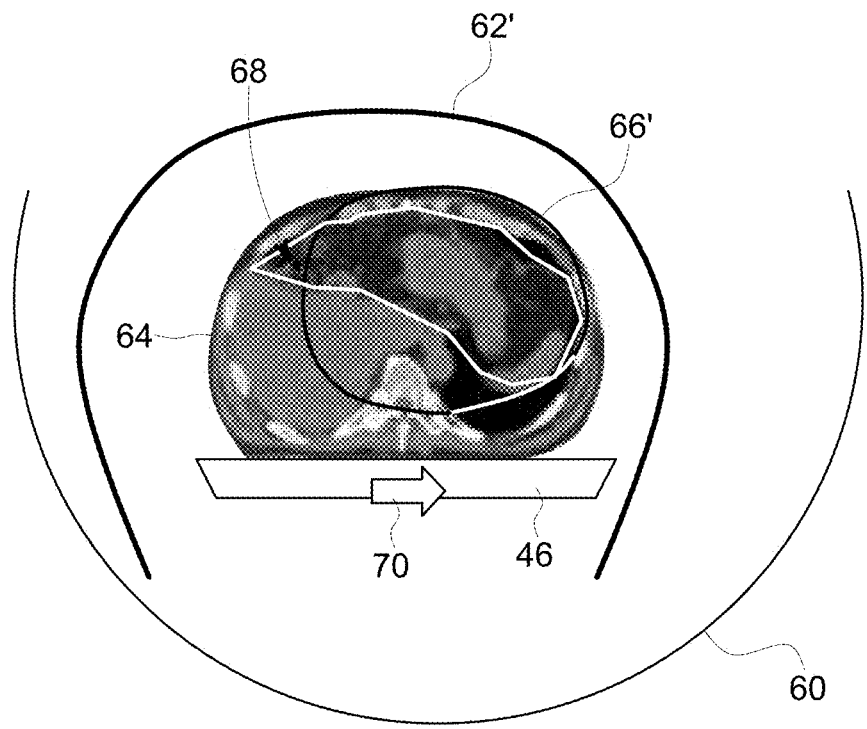

First, the semi-automated or user input based embodiment will be described herein. In an embodiment wherein user evaluation and input is to be received in producing the determined imaging system geometry, the field of view (FOV) resulting from the imaging system geometry determined at 106 is displayed at 108. The FOV is exemplarily overlaid upon the model of the patient as provided based upon the a priori patient information. FIG. 5A exemplarily depicts an exemplary embodiment of this graphical presentation. More specifically a model of the patient, for example a CT image of the patient at the imaging plane is provided. On the patient model 64 and initial field of view 66 is identified. In an exemplary, but not limiting embodiment, the source trajectory 60 and the detector trajectory 62 are also provided on the graphical display for presentation to the user. The clinician is prompted at 110 whether or not to accept the presented field of view 66. In making this determination, the user first provides region of interest (ROI) information. Exemplarily, the ROI information provided may be an identification of the ROI for the imaging procedure. The clinician may exemplarily use a user input device for example a touch screen, mouse, or electronic stylus to identify the ROI 68 in the patient model 64. In other embodiments, the imaging system may be capable of segmenting particular organs within the image or patient model and the clinician may select a pre-segmented organ or region. In a still further embodiment, the user may use the knowledge of the ROI 68 in order to evaluate the suitability of the presented FOV 66 relative to the ROI 68. If the user provides an indication that the presented FOV 66 is not acceptable at 110, then at 114 the system adjusts the FOV 66 to the ROI 68. In making such an adjustment, the user may provide inputs, for example in a drag and drop style of input to provide a new FOV 66'. In addition to user inputs, the adjustment of the FOV 66 to the ROI 68 at 112 may further include calculating a new trajectory for one or more of the x-ray source and the x-ray detector.

In the exemplary embodiment described herein, for the sake of simplicity, only the detector trajectory 62 is changed while the source trajectory 60 is maintained. It will be recognized that in other embodiments only the source trajectory may be changed or both the source trajectory and the detector trajectory may be modified. As explained in further detail herein by varying the trajectory of the detector (e.g. varying the OID) during the imaging procedure a contour of the patient may be followed which may be shaped to better accommodate the ROI 68. As depicted in FIG. 5a, adjustment of the FOV at 112 to the FOV 66', places a portion of the FOV 66' outside of the contour of the patient model 64. Therefore, in addition to the adjustment of the detector trajectory 62' in the imaging system geometry, a movement of the table 46, for example in the direction of arrow 70 repositions the patient within the detector trajectory to maximize the coverage of the ROI 68 with the FOV 66'. This is exemplarily depicted in FIG. 5b.

It will be recognized that in an additional exemplary embodiment of an automated or semi-automated method as described herein that the adjusted detector trajectory 62' may alternatively be calculated based upon the contour of the patient model 64. In such an exemplary embodiment, the detector trajectory 62' may be calculated for example to position the detector a constant distance from the contour of the patient within the other mechanical and geometric constrains on the imaging system. Such an embodiment may operate in the manner described herein to further refine the imaging geometry from that initial trajectory.

Figure 5C:
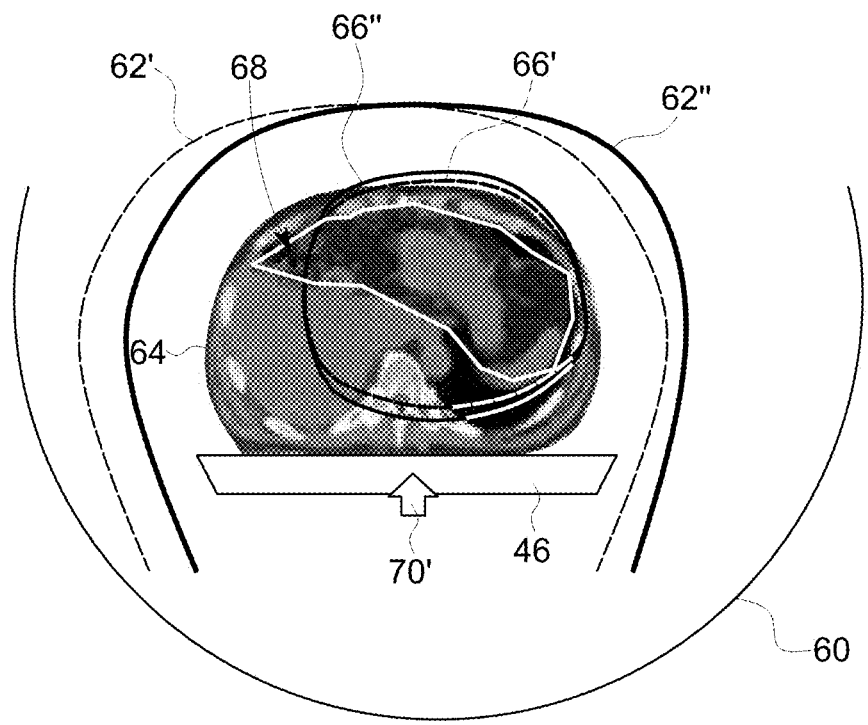
Figure 5D:
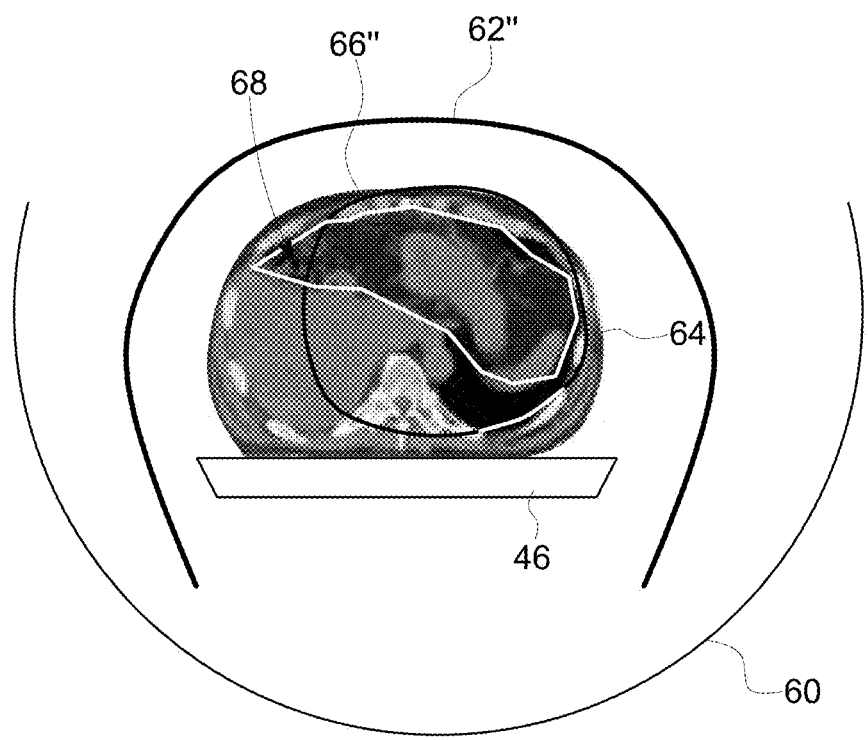

The method 100 may then operate to display the recalculated FOV 66' at 108 and prompt the user to accept the modified FOV 66' and the associated imaging system geometry. In the exemplary embodiment, the user may provide further input as to the shape of the FOV, for example to modify the shape of the FOV 66', for example to 66" as depicted in FIG. 5c. In response to this input and/or adjustment to the FOV at 112, the method may calculate a further detector trajectory 62" and a resulting table movement 70 in order to maximize coverage of the patient 64 and the ROI 68 with the FOV 66". The FOV 66" may be displayed to the user for acceptance, such as is depicted in FIG. 5d. In an exemplary embodiment, the user, when prompted at 110 provides an input of acceptance to the imaging system and at 116 the medical images are obtained using the source trajectory 60 and the detector trajectory 62" as exemplarily presented in FIG. 5d.

Now exemplarily referring to an automated implementation of an exemplary embodiment of the method 100, the determination of the imaging system geometry at 106 further initially includes information regarding the region of interest at 112. The information regarding the region of interest, as noted above, may include a detection of an organ to be imaged, in the exemplary embodiment described herein, such organ being a liver. Using image segmentation techniques, the ROI 68, which may be an organ to be imaged may be automatedly detected in the patient model 64 and/or other a priori information. The determination of the imaging system geometry at 106 may therefore start with an initial FOV 66 and detector trajectory 62, and with the incorporation of the ROI information 68, position an isocenter of the imaging system geometry at the location wherein the FOV 66 is positioned on the ROI 68. The imaging system geometry may include positioning of the table 46 to provide such positioning of the isocenter and to adjust the detector trajectory in a manner such as to minimize OID while avoiding collision between the detector and the table 46 or patient 64. As noted above, the contour of the patient model 64 may further be considered or incorporated, for example, to provide a trajectory that follows or at least partially follows the contour of the patient model 64. Such trajectory being exemplarily depicted in FIG. 5a as trajectory 62'. The adjustment of the detector trajectory 62' may exemplarily result in the FOV 66'. The new FOV 66' may require a further refinement of the table position, exemplarily requiring movement of the table in the direction of arrow 70, while still avoiding collision between the detector trajectory 62' with the table 46 and/or patient 64 this refinement, while producing data and/or image files capable of being presented may not require the actual visual display of the FOV, such as exemplarily described above with respect to 108.

At 110, the FOV 66' is evaluated for acceptance. This evaluation may be performed by application of at least one FOV optimization criteria at 118. If the FOV optimization criteria, exemplarily as described herein are met, then the method 100 may accept the currently presented FOV, if the FOV optimization criteria indicates that further refinement of the FOV is warranted, then the method will reiterate in the manner as described in further detail herein to refine the FOV. In an exemplarily embodiment, the FOV optimization criteria may exemplarily include a percentage of the ROI contained within the FOV. In an exemplarily embodiment, the system iterates to refine the FOV in a manner until 100 percent of the ROI is included within the FOV or the coverage of the ROI within the FOV is maximized. Similarly, the FOV optimization criteria may seek to minimize the portion of the ROI 68 which is not covered by the FOV 66'. In still further exemplarily embodiments, other considerations, for example, minimization of FOV outside of the contour of the patient model 64 is minimized and/or the FOV is optimized to minimize the maximum OID in the detector trajectory. In a still further exemplarily embodiment, the FOV optimization criteria 118 may further include a particular percentage improvement in an evaluated parameter, for example, the method may iteratively modify the FOV until there is a less than one percent improvement in the coverage of the ROI by the FOV. Although, it will be recognized that this improvement criteria is merely exemplarily and that a person of ordinary skill in the art would recognize other minimum improvement values as may be used in other embodiments.

In the example depicted herein, the FOV 66' may be adjusted to FOV 66' after the detector trajectory 62' is recalculated as detector trajectory 62" in an effort to center the patient within the source trajectory 60 and the detector trajectory 62". This may further result in movement of the table in the direction of arrow 70' to a new table position. These modified imaging system geometries including the source trajectory 60, detector trajectory 62", and the associated table position may be reevaluated at 110 against the FOV optimization criteria 118 and exemplarily accepted at which point the refined imaging system geometry is used to obtain the images of the patient at 116. It will be recognized that in exemplary embodiments, as noted above, that the source trajectory 60 may also be adjusted as part of the imaging system geometry within embodiments of the method 100. As an increase in SOD reduces radiation dose to the patient, in a further exemplary embodiment, the imaging system geometry may further include adjustment of the source trajectory in order to maximize SOD while achieving FOV coverage of the ROI.

It will be recognized that in embodiments the SID distance is adjustable during an imaging operation and is constrained by a rate at which the source and/or detector can be moved by the adjustable joint of the gantry without causing blurring or other artifacts in the acquired images. In an exemplary embodiment wherein both the detector trajectory and the source trajectory are variable during the imaging process, effective rates of change in the SID may be achieved while maintaining imaging quality by simultaneously moving the source and the detector either towards each other or away from each other along the respective trajectories.

Figure 6A:
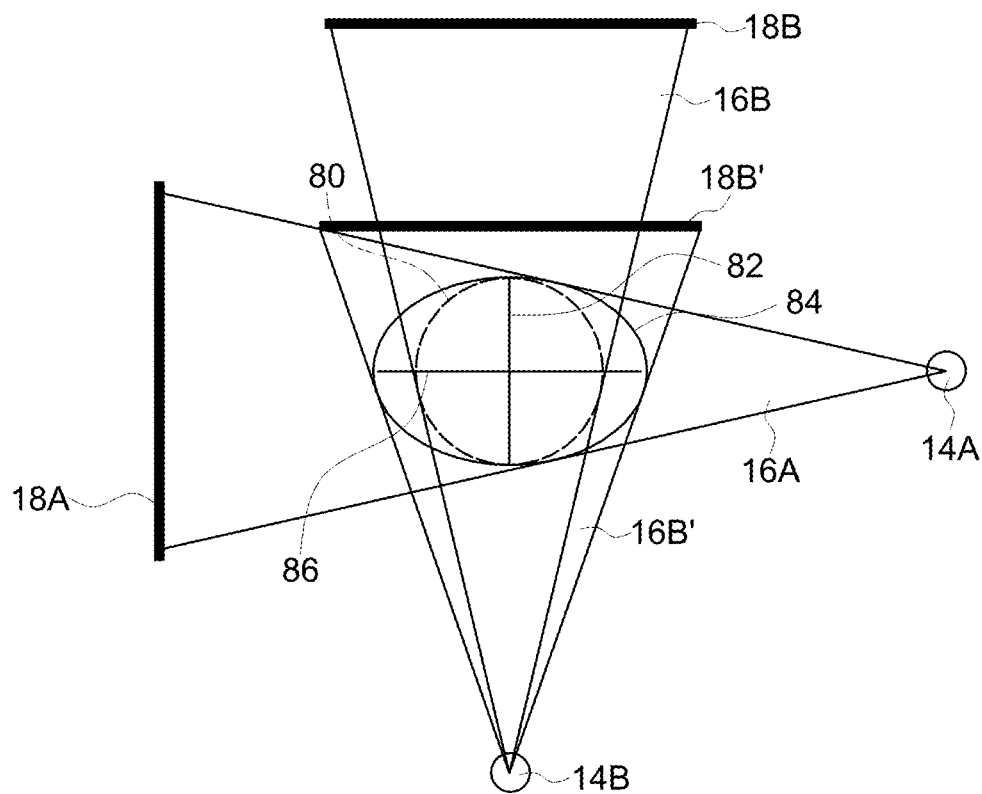
FIG. 6A depicts 3D fields of view for two exemplary imaging systems.
Figure 6B:
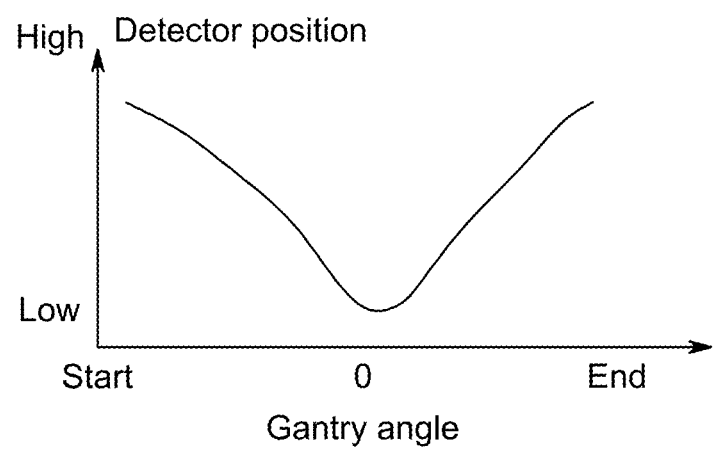
FIG. 6B is a graph of exemplary detector position versus gantry angle during an imaging procedure.

As exemplarily depicted in FIGS. 6A and 6B, the variation in the detector position during an imaging procedure can achieve a greater 3D field of view in a noncircular 3D reconstruction slice using a comparably sized detector. While increases in detector size can result in greater 3D FOV from an imaging procedure, increases in detector size come at comparatively great expense and further increase the geometrical constraints on the imaging system, increasing the potential for collisions between the detector and the patient or table. Therefore, embodiments of SID variable imaging with FOV optimization as provided by systems and methods as described herein can provide improved 3D FOV without increasing detector size.

FIG. 6A exemplarily depicts two imaging systems and the resulting 3D fields of view. FIG. 6A exemplarily depicts the source 14A at a starting position in the source trajectory (not depicted which projects an x-ray beam 16A to the detector 18A also exemplarily at the start position. The x-ray source 14B exemplarily represents a midpoint of the gantry rotation also corresponding to detector 18B with beam 16B representing the x-ray beam therebetween during the imaging procedure. In this exemplarily embodiment, the detector 18A, 18B represents the 2D field of view available during the imaging procedure which in a merely exemplary embodiment is about 40 cm. In the embodiment depicted, the SID remains constant through the imaging procedure at an exemplarily 129.5 cm. The SOD also remains constant at an exemplary 83 cm. This results in 3D field of view 80 having a diameter 82 of exemplarily 24 cm.

FIG. 6B depicts an exemplarily graph of detector position versus gantry angle during an imaging procedure. The detector position may exemplarily be represented in terms of OID or SID depending upon the particular embodiment of the systems and methods as described herein. As can be seen from the exemplarily graph in FIG. 6B, the detector is moved closed to the object and/or the x-ray source and then moved away again during the imaging procedure. This movement of the detector is exemplarily depicted in FIG. 6A by the position of detector 18B', which exemplarily represents a detector position at a midpoint of the imaging procedure in an embodiment wherein the detector has a variable detector trajectory. X-ray source 14B is similarly positioned along the source trajectory at the midpoint of the imaging procedure and projects x-ray beam 16B' at the detector 18B'. While the 2D field of view represented by the detector 18B' remains the same at about 40 cm., the SID is exemplarily reduced to 99 cm which widens the resulting 3D field of view 84 in the horizontal dimension 86 exemplarily to 32 cm. The result is that a larger 3D field of view is achieved with the same physical detector size. Exemplarily FOV 80 has an area of 452 sq. cm. while the area of FOV 84 is exemplarily ⅓ larger at 603 sq. cm. Thus, through the use of systems and methods as described herein, not only can the effective 3D FOV be increased, but the imaging system geometry adjusted to maximize the coverage of the ROI with the available FOV.

In further exemplarily embodiments, the trajectory of the x-ray source and/or x-ray detector may be further combined with a trajectory of the entire C-arm itself or the table during the imaging procedure. A further C-arm trajectory or table trajectory in the manners as previously described above, would effectively adjust the isocenter of the imaging during the imaging procedure. In still further embodiments, this may be used to further enable to detector trajectory and/or source trajectory to follow the contours of the patient and to further refine the 3D FOV from the imaging procedure to better match the ROI within the patient.

It will be recognized that while exemplarily embodiments herein have been described with respect to a 3D FOV, in some embodiments, 2D projection images as depicted and described herein may be acquired and used for their own purpose and imaging part from the construction of a 3D reconstructions. It will be recognized that similar techniques and advantages may be applied and found in these embodiments as well, including, but not limited to those embodiments wherein the source is an imaging modality different from the x-rayed imaging modalities typically used in CT 3D reconstruction.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for imaging:
   gantry movable relative to a subject, the gantry comprising at least one adjustable joint;
   a source configured to emit radiation during an imaging procedure;
   a detector configured to receive attenuated radiation from the source during the imaging procedure, at least one of the source and the detector movable relative to the other by the at least one adjustable joint of the gantry; and
   an imaging controller operably connected to at least the gantry and to the adjustable joint, wherein the imaging controller receives a priori subject information that includes a patient contour and imaging system geometry information, prior to the imaging procedure the imaging controller determines an imaging geometry based upon the received patient contour and imaging system geometry information and operates the gantry and the at least one adjustable joint to vary a source to image-receptor distance (SID) according to the imaging geometry during the imaging procedure.

2. The system of claim 1 further comprising a movable subject support operably connected to the imaging controller, wherein the system geometry further comprises a position of the movable subject support and the imaging controller operates the movable subject support to the position for the imaging procedure.

3. The system of claim 1, wherein the subject is a patient, the source is an x-ray emitter, and the detector is an x-ray detector and the imaging controller acquires medical images in the form of x-ray images during the imaging procedure.

4. The system of claim 3, wherein the x-ray emitter is movably secured to the gantry by an emitter joint and the x-ray detector is movably secured to the gantry by a detector joint.

5. The system of claim 4, wherein the emitter joint and the detector joint are both operable by the imaging controller to adjust the SID during the imaging procedure.

6. The system of claim 3, wherein the x-ray emitter is a cone-beam emitter and the acquired medical images are projection images.

7. The system of claim 6, wherein the imaging controller further receives the projection images and produces at least one three-dimensional (3D) reconstructed image from the projection images.

8. The system of claim 1, wherein the imaging geometry comprises a source trajectory and a detector trajectory.

9. The system of claim 1, further wherein the imaging controller further receives a region of interest, determines a field of view (FOV) of the imaging procedure based upon the region of interest and adjusts at least one of a source trajectory and a detector trajectory of the imaging geometry based upon the FOV.

10. The system of claim 9, further comprising:
a graphical display operated by the imaging controller to visually present the region of interest, FOV, and the imaging geometry to a user; and
a user input device operable by the imaging controller to receive user inputs to adjust at least one of the region of interest, FOV and imaging geometry;
wherein upon receiving the user inputs, the imaging controller modifies the imaging geometry according to the user inputs.

11. A method of medical imaging, comprising:
obtaining patient information of a patient to be imaged;
determining a patient contour from the patient information;
determining a field of view (FOV) for an imaging procedure according to the patient information;
determining an imaging geometry at least in part based upon the FOV and the patient contour, the imaging geometry comprising at least one of an emitter trajectory and a detector trajectory with a variable source to image-receptor distance (SID) between the emitter trajectory and the detector trajectory;
evaluating the FOV by applying at least one FOV optimization criteria to the FOV;
adjusting the FOV to a region of interest of the patient to be imaged according to the evaluation of the FOV; and
adjusting the imaging geometry to the adjusted FOV.

12. The method of claim 11, wherein the patient information is a digital model of the patient to be imaged.

13. The method of claim 11, further comprising:
presenting the FOV on a graphical display in combination with the patient information;
receiving a user input at a user input device associated with the FOV; and
adjusting the imaging geometry from the user input.

14. The method of claim 11, further comprising obtaining imaging system geometry information wherein at least one of an emitter trajectory and a detector trajectory is determined in part based upon the imaging system geometry information.

15. The method of claim 11, further comprising obtaining medical images with an imaging procedure after adjusting the imaging geometry to the adjusted FOV.

16. The method of claim 15 wherein the obtained medical images are x-ray images.

17. The method of claim 11, further comprising obtaining region of interest information, wherein the FOV is adjusted based upon the region of interest information.

18. The method of claim 17, wherein the region of interest information used to determine at least one of an emitter trajectory and a detector trajectory.

19. The method of claim 17, wherein at least one FOV optimization criteria comprise maximizing the region of interest covered by the FOV.

* * * * *